US00PP08562P

United States Patent [19]

Drewlow

[11] Patent Number: Plant 8,562

[45] Date of Patent: Jan. 25, 1994

[54] POINSETTIA PLANT NAMED DASHER

[75] Inventor: Lyndon W. Drewlow, Ashtabula, Ohio

[73] Assignee: Mikkelsens, Inc., Ashtabula, Ohio

[21] Appl. No.: 22,345

[22] Filed: Feb. 24, 1993

[51] Int. Cl.[5] ..... A01H 5/00

[52] U.S. Cl. ..... Plt./86.4

[58] Field of Search ..... Plt. 864

*Primary Examiner*—James R. Feyrer

*Attorney, Agent, or Firm*—Foley & Lardner

[57] ABSTRACT

A new and distinct cultivar of poinsettia plant named Dasher, produced by grafting a seedling from the cross described to a plant of Super Rochford for the purpose of transferring the excellent branching characteristics of Super Rochford. Dasher is characterized by its red, relatively large bracts, strong, vigorous growth habit, early flowering, excellent branching, excellent foliage retention, resistance to heat delay of flower bud initiation when night temperatures are above 23° C., dark green leaves, and small cyathia cluster.

2 Drawing Sheets

The present invention relates to a new and distinctive cultivar of poinsettia plant, botanically known as *Euphorbia pulcherrima*, and referred to by the cultivar name Dasher.

Dasher was developed by me through controlled breeding by crossing Mikkelsen Seedling No. 86-167-1 (seed parent) with Mikkelsen Seedling No. 86-166-1 (pollen parent). The new seedling, characterized by red bracts and poor branching, was identified by No. 88-216-1. This seedling was then grafted to the excellent branching type cultivar Super Rochford (not patented) in an attempt to transfer the branching habit of Super Rochford to the new seedling. The graft was successful, resulting in the seeding having the braching habit of Super Rochford and retaining all other desirable characteristics of the new seedling.

A sexual reproduction by stem cuttings in a greenhouse in Ashtabula, Ohio has shown that the unique features of this new poinsettia are stabilized and are reproduced true to type in successive propagations.

The following characteristics distinguish Dasher from both its parent cultivars and other cultivated poinsettia of this type known and used in the floriculture industry.

1. When 5 or more nodes are left after a pinch (apical tip removal) Dasher will develop full length shoots from each node like Super Rochford, and Feliz Navidad (plant patent pending), while the original seedling 88-216-1 will develop a full length shoot only from the upper 2 or 3 nodes, with the balance of shoots being greatly repressed.

2. Dasher at 20 to 22 cm is shorter than the 88-216-1 seedling at 25 to 27 cm when similar size plants are left after pinching, because there is little or no apical dominance in the branched types. Thus, lower breaks may grow longer than top breaks on a plant instead of 2 or 3 shoots becoming dominant. Super Rochford is taller at 30 to 32 cm, as in Feliz Navidad at 26 to 28 cm.

3. Dasher has dark green leaves (139A) which are slightly lighter than the original seedling 88-216-1, but not as dark as Lilo (U.S. Plant Pat. No. 6,694). Super Rochford and Feliz Navidad have leaves which are a more yellow green 147A in color.

4. Dasher is more tolerant than 88-216-1 to low light levels and high temperatures of the average home as leaves do not yellow and drop like 88-216-1 under these conditions. When kept moist, Dasher has excellent foliage retention, similar to the comparison cultivars.

5. Bract coloration of Dasher is between 45D and 47A, which is a ligther red than the bract color (between 45C and 47A) of seedling 88-216-1, but darker than the bracts of Feliz Navidad (45B to 45C).

6. Dasher has a cyathia cluster (flowers in center of bract) that is slightly smaller in number and diameter (2–3 cm) than the original seedling 88-216-1; smaller than Lilo and Super Rochford, and similar to Feliz Navidad.

7. Dasher is resistant to heat delay of flower bud initiation when night temperatures are above 23° C., similar to 88-216-1 and Feliz Navidad, with Super Rochford and Lilo being very susceptible to heat delay. This is of commercial importance, especially in the southern U.S.A. and warmer than normal autumns in the north.

8. Bract size of Dasher at 25 to 28 cm is larger that Lilo and Super Rochford at 20 to 23 cm, but not as large as Feliz Navidad at 30 to 32 cm. Bracts are somewhat upward facing while Feliz Navidad has a more reflexed bract and Super Rochford and Lilo have flat bracts. Cyathia will not split apart like Super Rochford and Lilo but remain in a tight cluster at center like Feliz Navidad.

9. All other characteristics of Dasher are similar to the original seedling, 88-216-1, such as early flowering under natural short days, similar shaped leaves and bracts, and retention of cyathia under stress conditions.

The accompanying colored photographs illustrate the overall appearance of Dasher, and show the colors as true as is reasonably possible to obtain in colored reproductions of this type. The photograph on sheet 1 is a front perspective view showing the bracts and foliage of a typical plant of Dasher. The photograph on sheet 2 is a top perspective view of the plant, showing the bracts more clearly. The photographs were taken on Nov. 26, 1991 in a rigid fiberglass greenhouse on an overcast day in Ashtabula, Ohio.

The following detailed description of my new cultivar is based on plants produced in greenhouses in Ashtabula, Ohio during the Fall season of the year. Plants were grown in 15 cm pots and measurements were taken seventeen (17) weeks after rooted cuttings were planted. Height measurements were taken from the soil line of the container. The plants were grown at 64°-68° F. night temperatures, under 3500-4000 foot candles of light, and with 250 ppm Nitrogen, 75 ppm Potassium, and 250 ppm Phosphorous nutritional levels, with trace elements added. Habit of growth, foliage coloration, leaf variegation, size of leaves and flower size will be influenced by nutritional and environmental conditions, without, however, any variation in genotype.

Color references are made to The Royal Horticultural Society Colour Chart except where general terms of ordinary dictionary significance are used.

Parentage: Controlled cross between female Mikkelsen Seedling No. 86-167-1 and male Mikkelsen Seedling No. 86-166-1; resulting seedling (88-216-1) then grafted to a plant of Super Rochford.

Propagation:

A. *Type cutting.*—Stem 5 to 6 cm long.

B. *Time to root.*—14 days at 21° C. Summer; 18 days at 21° C. Winter.

C. *Rooting habit.*—Abundant, thick, fibrous roots.

Plant Description:

A. *Form.*—Upright; when apical meristem is removed (pinching) leaving 5 or more nodes above soil line of pot, generally all lateral shoots will emerge and develop, compact in nature.

B. *Habit of growth.*—Strong, thick stems with strong branch angles hold bracts up for good display of color. Bottom stems break first and elongate faster than upper stems, resulting in the upright growth habit with bract display on upper ⅔ of plant. Growth is vigorous so that plants of Dasher can easily be grown with use of proper scheduling system without chemical growth regulators.

C. *Foliage.*—Leaves are alternate and borne on 3.0 to 4.0 cm long petioles with a reddish purple cast; last 3-4 leaves before true bract leaves also turn same red color as bracts. 1. Size: Mature leaves are 10 to 12 cm long and 8 to 9 cm wide at broadest point near basal area of leaf. 2. Shape: Ovate with acuminate apex and rounded base. 3. Texture: Upper glabrous; lower glabrous and rugose because of protruding veins. 4. Margin: Entire. 5. Color: Young foliage, top side, 144A. under side, 146B. Mature foliage, top side, 139A. under side, 146A.

Flowering Description:

A. *Flowering habits.*—earlier flowering than most older commercial cultivars. Dasher appears to have a longer critical daylength for flower initiation. Under controlled daylength, development time is approximately 8½ weeks and appears even earlier because last 3 or 4 true leaves turn red before bract fully develops. The early flower initiation is of commercial significance. Bracts in involucre face somewhat upward.

B. *Natural flowering season.*—November 15 to 22 under Ohio conditions. Flowering time under 11 hours of daylength at 20° C. is 8½ weeks. Dasher does not heat delay (failure to set flower bud under night temperature above 23° C.).

C. *Cyathia description.*—Few in number in tight cluster at center of bract; are stress tolerant, remaining in the involucre for a considerable time under low fertility, low light, high temperature conditions even after pollen shed. Severe drying may cause them to drop.

D. *Cyathia borne.*—Stay closely clustered without growing apart (splitting). Usually 2 to 3 cm in diameter. Flowering can be initiated any time of the year by controlling the daylength to approximately 11 hours total. Cyathia will continue to initiate until daylength is greater than approximately 13 hours.

E. *Quantity of cyathia.*—Highly dependent on cultural practices and can vary from minimum of 3 to 4 to more than 10.

F. *Bracts.*—1. Shape: Ovate. First bracts 9 to 10 cm long and 5 to 6 cm wide, on 1.0 to 1.5 cm petioles; later bracts are 6 to 7 cm long and 4.0 to 5.0 cm wide on 0.5 to 1.0 cm petioles. 2. Color at maturity: Between 45D and 47A, young bract 45C; under side between 45C and 47A, with midrib and major veins being greenish in color. 3. Number of bracts: 10 to 15 normal number but could be fewer or more depending on growing conditions. Bract diameter varies with growing conditions, for example, if plants are pinched and growth regulators are used.

G. *Reproductive organs.*—1. Stamens: numerous. a. Anther shape: oblong, color reddish. b. Filament color: reddish. c. Pollen color: yellow. 2. Pistels: a. Stigma shape: forked, color reddish. b. Style color: reddish. c. Ovaries: Celled, 3 in number, 3 mm when stigma is receptive, green. 3. Nectar cups: Generally 2 nectar cups on each cyathia, with none or 1 occurring rarely; nectar readily available on maturing cyathia.

Disease resistance: Bracts are resistant to botrytis damage, even on older bracts and pollen shed. Small cyathia area helps prevent botrytis after nectar cups start exuding honey-like substance.

Other Important Characteristics

A. Upright growth habit with strong stems and excellent branch angles hold up bracts well and make Dasher excellent for faster and easier sleeving for shipping with a minimum of breakage.

B. Early flowering under natural short day conditions eliminate the need for black cloth for mid-November sales.

C. Dark green foliage gives plant a healthy look.

D. Due to its compact growth habit, proper scheduling permits Dasher to be grown without growth regulators, thereby eliminating both a crop expense and a potential environmental hazard.

I claim:

1. A new and distinct cultivar of poinsettia plant named Dasher, as illustrated and described.

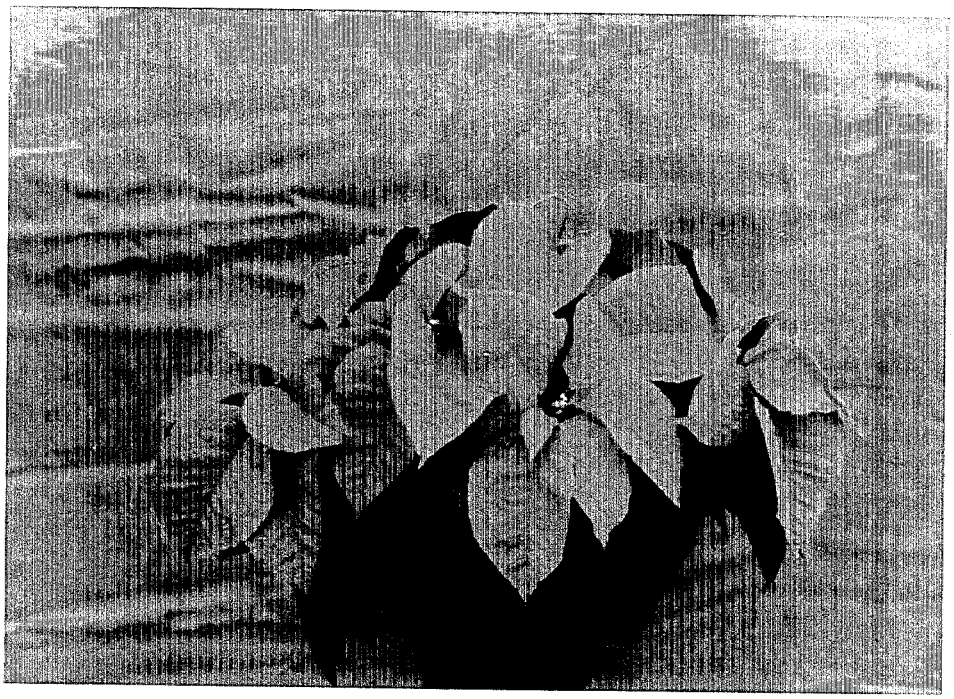

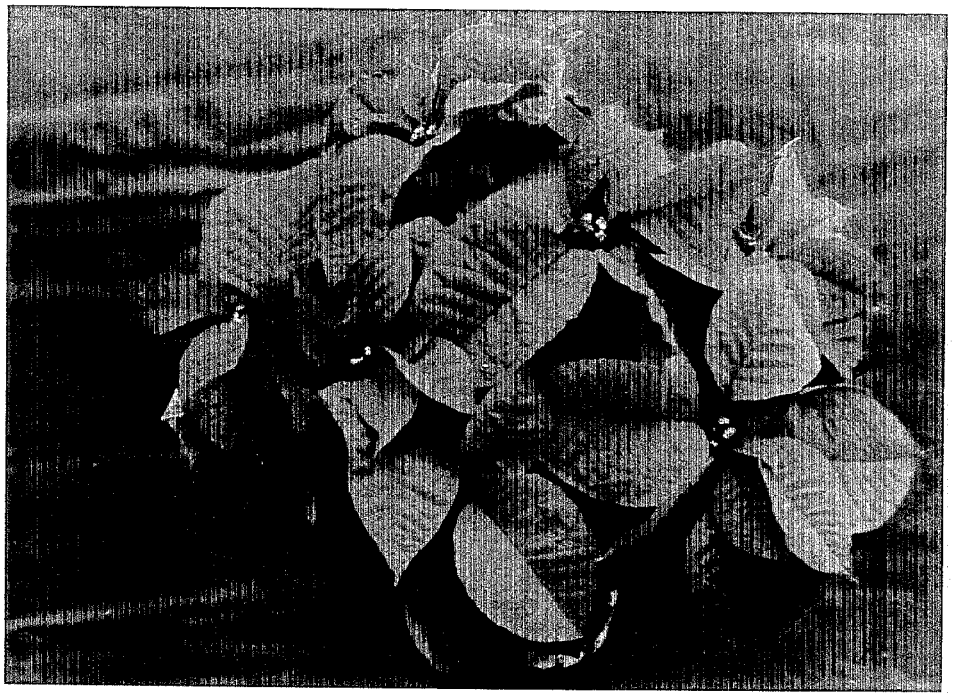

* * * * *